United States Patent [19]

Summers

[11] Patent Number: 5,458,573
[45] Date of Patent: Oct. 17, 1995

[54] EVERTING TOPOSCOPIC DILATION CATHETER

[75] Inventor: David P. Summers, The Woodlands, Tex.

[73] Assignee: American BioMed, Inc., The Woodlands, Tex.

[21] Appl. No.: 877,522

[22] Filed: May 1, 1992

[51] Int. Cl.$^6$ .................................................. A61M 29/00
[52] U.S. Cl. .............................. 604/101; 604/53; 604/271
[58] Field of Search .................................... 606/191–192, 606/194; 604/96, 101, 271, 53, 95

[56] References Cited

U.S. PATENT DOCUMENTS

| | | | |
|---|---|---|---|
| 3,435,826 | 4/1969 | Fogarty | 606/194 |
| 3,831,587 | 8/1974 | Boyd | 128/6 |
| 4,271,839 | 6/1981 | Fogarty et al. | 604/271 X |
| 4,526,175 | 7/1985 | Chin et al. | 604/271 X |
| 4,732,152 | 3/1988 | Wallstén et al. | 604/271 X |
| 4,762,130 | 8/1988 | Fogarty et al. | 606/194 X |
| 4,820,270 | 4/1989 | Hardcastle et al. | 604/96 |
| 4,848,343 | 7/1989 | Wallstén et al. | 604/271 X |
| 4,946,440 | 8/1990 | Hall | 604/95 |
| 5,074,845 | 12/1991 | Miraki et al. | 604/101 |
| 5,102,415 | 4/1992 | Guenther et al. | 606/159 |

*Primary Examiner*—Corrine M. Maglione
*Attorney, Agent, or Firm*—Gunn & Associates

[57] ABSTRACT

The present invention is directed to a toposcopic dilatation catheter system utilizing a dilatation balloon in combination with an everting tube in a miniature catheter of a scale sufficiently small to negotiate a blood vessel for therapeutic as well as diagnostic purposes. The catheter system utilizes a primary catheter shaft provided with multiple lumen or passageways extending the length thereof. The dilatation balloon lumen provides access to a balloon carried at the distal end of the primary catheter shaft. The dilatation balloon may be expanded as required to aid in advancing the catheter system to the site requiring therapy. A secondary catheter tube is coaxially carried within the primary catheter shaft. The leading end of the secondary catheter tube includes an everting tube which everts from the leading end of the primary catheter shaft. The everting tube advances under fluid pressure in advance to the leading end of the primary catheter shaft. In an alternate embodiment, thumb actuated actuator wire is carried in a third lumen extending along the length of the primary catheter shaft. The actuator wire enables the leading end of the primary catheter shaft to be guided into a blood vessel branch or along a narrow tortuous blood vessel. In another alternate embodiment, a secondary dilatation balloon is carried on the distal end of the secondary catheter in advance of the everting tube. The secondary tube may be used to canalize, dislodge and remove a blood clot.

8 Claims, 4 Drawing Sheets

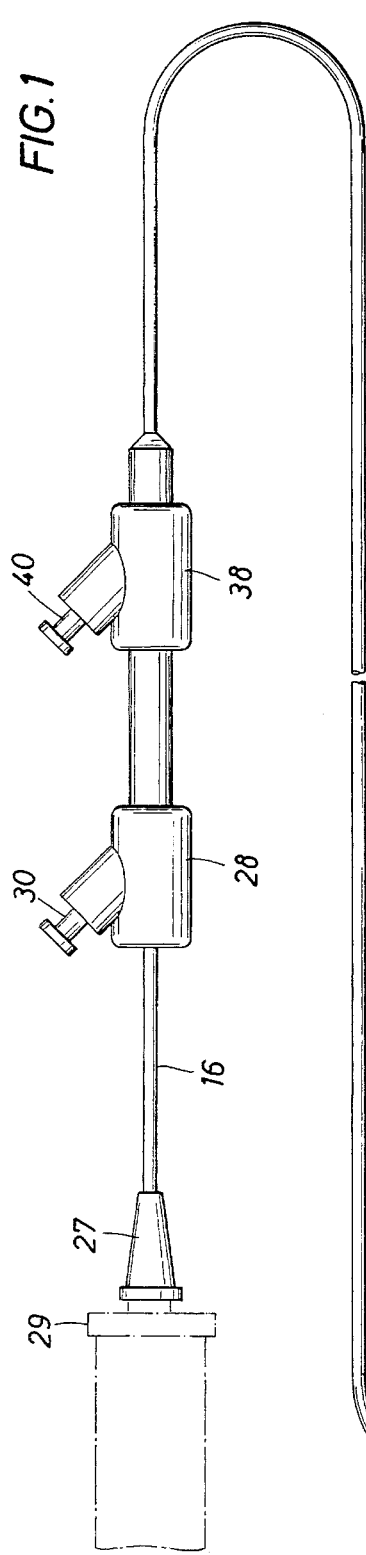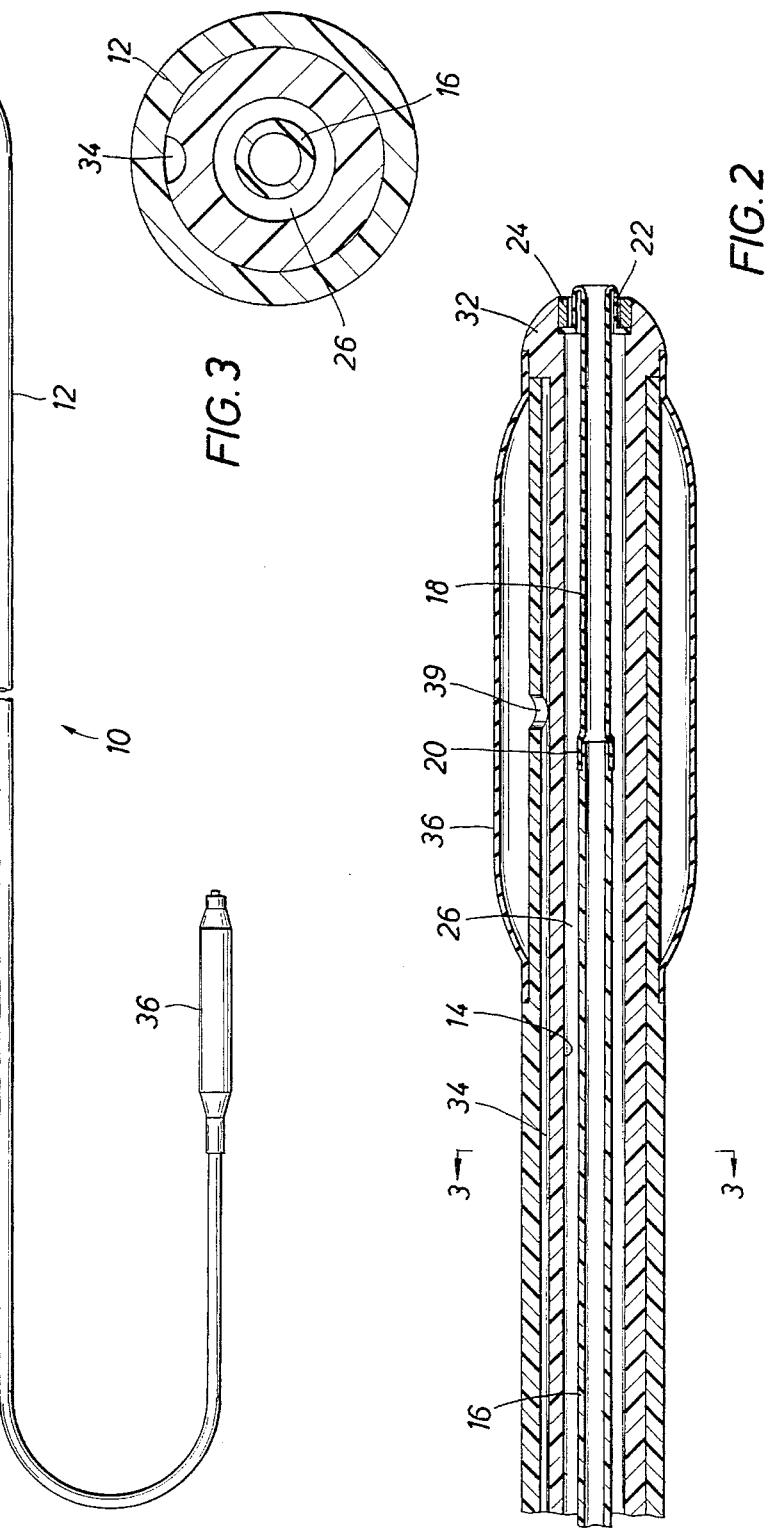

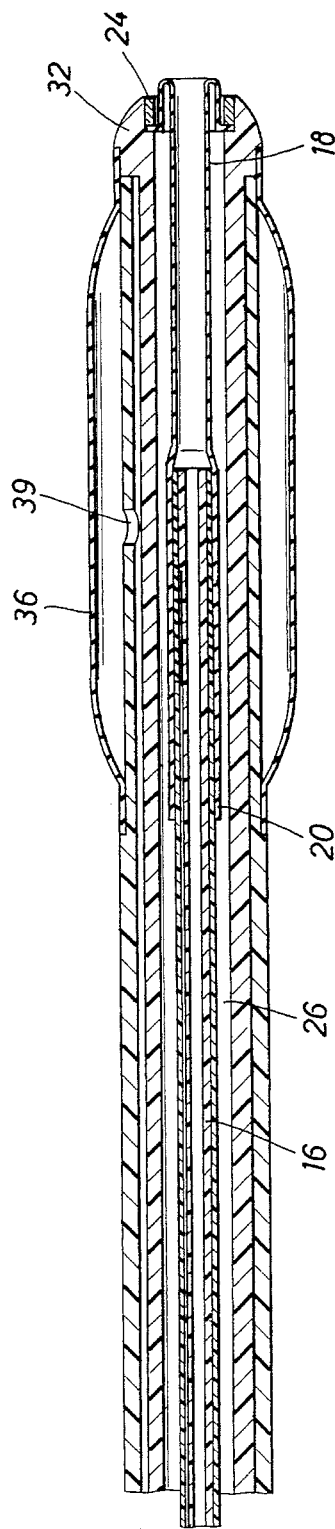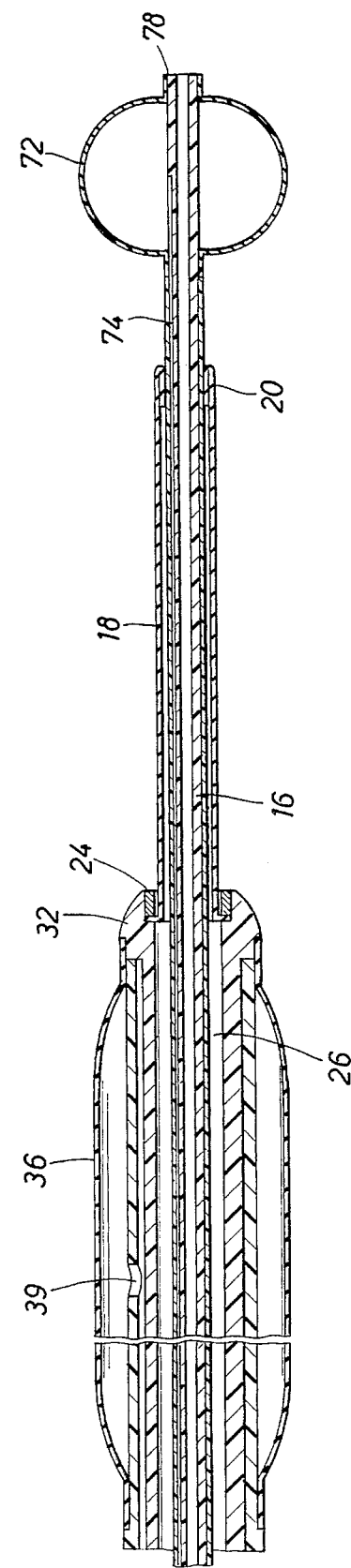

EVERTING TOPOSCOPIC DILATION CATHETER

BACKGROUND OF THE DISCLOSURE

The present invention is directed to a dilatation catheter, particularly, a toposcopic balloon dilatation catheter for use in the distal and coronary arteries where small vessel size and tortuosity present numerous problems of access.

Many technological advancements have been made in recent years in the treatment of coronary disease. For example, various prior art devices have been developed for removing and/or compressing atherosclerotic plaque, thromboses, stenosis, occlusion, clots, embolic material, etc. from veins, arteries and the like. As noted in U.S. Pat. No. 4,437,857 to Goldstein, et al., catheter systems have previously been used to traverse and negotiate blood vessels for therapeutic as well as diagnostic purposes. Catheter systems have been used to deliver chemotherapeutic agents and other substances to localized areas in the vascular system and to retrieve samples of body fluids from remote spaces. Balloon-type catheters, for example, have been used for treating stenoses in blood vessels as a means of relieving the constriction by physically expanding the vessel in the region of a stenosis. Catheter systems are also available for removal of occlusive material blocking coronary vessels. One such device is disclosed in the Applicant's U.S. Pat. No. 5,087,265 which utilizes a cutting element mounted on the distal end of a catheter for excising occlusive material from veins, arteries and the like.

While the usefulness of this form of treatment has been recognized, lesions requiring treatment are rarely easily accessible. Thus, efforts have been made to develop catheter systems which can successfully penetrate even deeper into the vascular system for treatment of remotely located lesions. In U.S. Pat. No. 4,437,857 a catheter system is disclosed for traversing blood vessels wherein the known principle of an everting tube is utilized in a miniature catheter of a scale sufficiently small to negotiate a blood vessel. The everting tube principle had previously been applied to catheters, however, such catheters generally were intended for use in relatively large scale body passages and would not have been suitable for use in an intravascular application requiring extensive penetration along extremely narrow and tortuous vessels. Even small blood vessels, however, may be partially or totally blocked so that the catheter cannot be advanced to the location requiring therapy.

Recently, special catheters have been designed to treat embolism of the peripheral vascular, both through instillation of thrombolytic and acute displacement and removal of both embolus and thrombus (more commonly known as blood clots). These catheters are designed to both penetrate and irrigate the problem clot. Most, if not all, depend upon a stiffening member either temporarily or permanently integrated into the catheter shaft providing the necessary stiffening and rigidity needed to pentract the clot.

It is therefore object of the instant invention to provide a method and apparatus for penetrating, irrigating, and removing said clots without the use of stiff and often dangerous stiffeners or stylets. This is accomplished by utilizing the self-canalizing effect of the everting mechanism of a toposcopic catheter to penetrate and bore through a clot without the application of compressive thrust or friction to the vascular structures.

It is another object of the present invention to provide a method and apparatus for traversing body passages, such as blood vessels and which allows relatively deep penetration of the vascular system even through narrow, totally or partially blocked blood vessels.

It is still another object of the present invention to provide a catheter system which combines the principle of balloon dilatation with the principle of an everting tube in a miniature catheter of a scale sufficiently small to negotiate a blood vessel.

It is yet another object of the present invention to provide an improved method and apparatus for traversing a blood vessel for therapeutic or diagnostic purposes.

SUMMARY OF THE INVENTION

The present invention is directed to a toposcopic dilatation catheter system utilizing a dilatation balloon in combination with an everting tube in a miniature catheter of a scale sufficiently small to negotiate a blood vessel for therapeutic as well as diagnostic purposes. The catheter system utilizes a primary catheter shaft provided with multiple lumen or passageways extending the length thereof. The dilatation balloon lumen provides access to a balloon carried at the distal end of the primary catheter shaft. The dilatation balloon may be expanded as required to aid in advancing the catheter system to the site requiring therapy. A secondary catheter slide tube is coaxially carried within the primary catheter shaft. The leading end of the catheter slide tube includes an everting tube which everts from the leading end of the primary catheter shaft. The everting tube advances under fluid pressure in advance of the leading end of the primary catheter shaft. In an alternate embodiment, a thumb actuated actuator wire is carried in a third lumen extending along the length of the primary catheter shaft. By application of either tension or compression to the actuator wire, the tip of the primary catheter may be deflected up to 180°. Alternatively, a shape memory alloy such as nickel titanium alloy may be placed within the wall of the catheter tip and with application of electrical current, sufficient heat is generated producing the desired deflection. The actuator wire enables the leading end of the primary catheter shaft to be guided into a blood vessel branch or along a narrow tortuous blood vessel. In another alternate embodiment, a second dilatation balloon is carried on the distal end of the catheter slide tube in advance of the everting tube.

DETAILED DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 1 is an elevational, partially broken away view of the dilatation balloon catheter system of the invention;

FIG. 2 is a sectional view of the forward end of the catheter system of the invention showing the everting tube fully retracted;

FIG. 3 is a sectional view taken along line 3—3 of FIG. 2;

FIG. 9 is a sectional view of the forward end of alternate embodiment of the catheter system of the invention wherein the everting tube is shown in a fully retracted position; and FIG. 10 is a sectional view of the forward end of the catheter system of the invention shown in FIG. 9 showing the everting tube in a fully extended position and the second dilatation balloon expanded.

DETAILED DESCRIPTION OF THE PREFERRED EMBODIMENT

Figure 4:
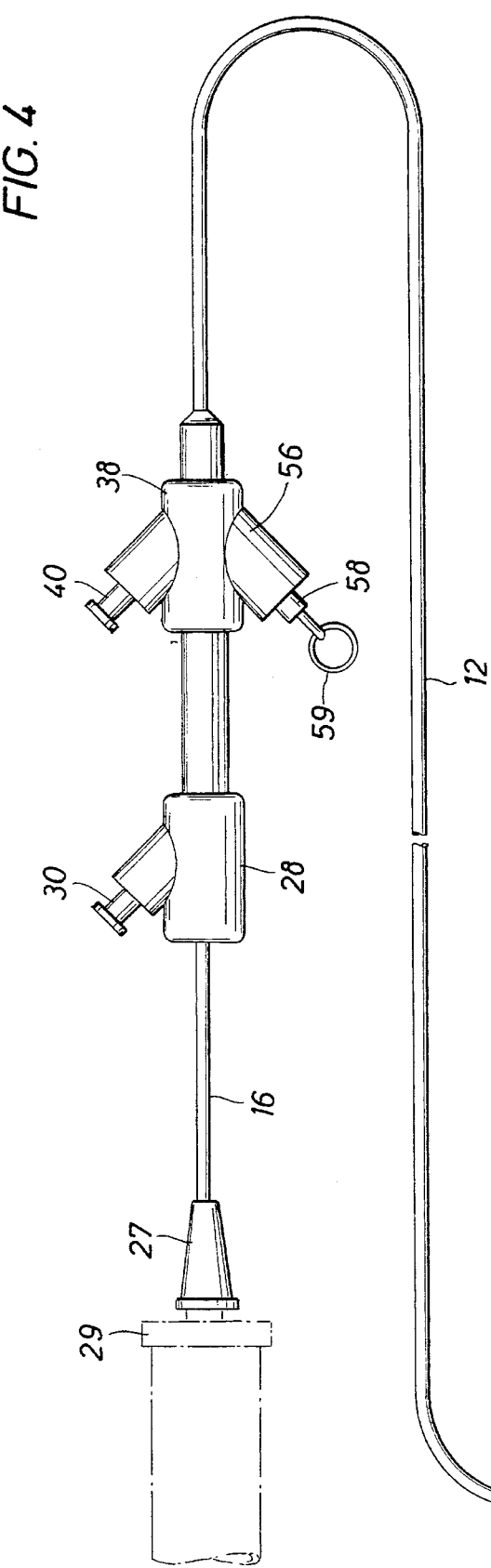
FIG. 4 is a elevational, partial broken away view of an alternate embodiment of the dilatation balloon catheter system of the invention.
Figure 5:
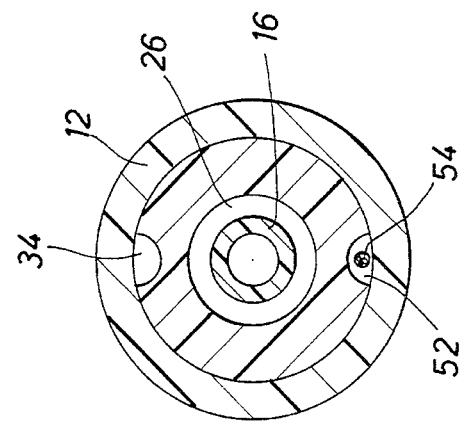
FIG. 5 is a sectional view taken along line 5—5 of FIG. 6.

Referring first to FIG. 1, the dilatation balloon catheter of the invention is generally identified by the reference numeral 10. The catheter 10 of the invention comprises a flexible primary or outer catheter shaft 12 which may be several feet in length. The catheter shaft 12 includes a through lumen 14. The slide tube 16 is hollow. A catheter slide tube 16 is housed within the catheter shaft 12 coaxially positioned in the lumen 14. An everting, flexible tube 18 connects the distal end of the catheter shaft 12 to distal end of the catheter tube 16. As more clearly shown in FIG. 2, the forward end of the slide tube 16 is fused or welded to the rear of the everting tube 18 at point 20. The forward end 22 of the everting tube 18 is fused or bonded to an insert clip 24. The end 22 of the everting tube 18 is pre-bonded to the insert clip 24, which is then inserted and bonded to the distal end of the catheter shaft 12. The lumen 14 is thus closed at its forward end by the everting tube 18 and an annulus 26 is defined between the outer wall of the slide tube 16 and the inner wall of the catheter shaft 12.

The proximal end of the everting slide tube 16 extends through a Y-fitting 28 and terminates at an end connector 27. The connector 27 is internally threaded for connection to a syringe 29 or other medical device for injection of fluid or medication through the slide tube 16. The annulus 26 is closed at the proximal end of the catheter shaft 12 by a seal assembly housed within the Y-fitting 28.

The Y-fitting 28 includes an angular passage which terminates at an outlet connection 30 for connection to a cannula or hypodermic needle. The angularly extending passageway is in fluid communication with the annulus 26.

The catheter shaft 12 and slide tube 16 are formed of conventional flexible catheter tubing used for intra-vascular applications, for example, polyethylene tubing several feet in length. The tubing is coated with a silicon lubricant for friction reduction. The leading end 32 of the catheter shaft 12 is tapered, enabling the catheter shaft 12 to be advanced through occlusive material which may be partially or totally blocking a blood vessel. The everting tube 18 is likewise formed of a flexible, synthetic, plastic material and covered with a friction reducing lubricant. The everting tube 18 is less stiff than the catheter shaft 12 and everting slide tube 16 so that it will advance beyond the leading end 32 of the catheter shaft 12 upon application of fluid pressure in the annulus 26.

The catheter shaft 12 is provided with a second lumen 34 which is axially offset from the lumen 14. The lumen 34 extends along the length of the catheter shaft 12 providing a fluid conduit for outward expansion of the dilation balloon 36. The balloon 36 is a flexible, plastomeric or rubber membrane which may be expanded to engage the arterial wall. A Y-fitting 38 mounted on the catheter shaft 12, in advance of the Y-fitting 28, seals the balloon lumen 34 and forms a fluid injection passageway therewith. The Y-fitting 38 is provided with a connection 40 for coupling to a fluid source or a syringe. Expansion of the balloon 36 is accomplished by injecting pressurized fluid in the lumen 34 which fills the balloon 36 through a port 39 formed through the outer wall of the catheter shaft 12. Upon release of fluid pressure, the balloon 36 deflates to its original configuration.

Figure 6:
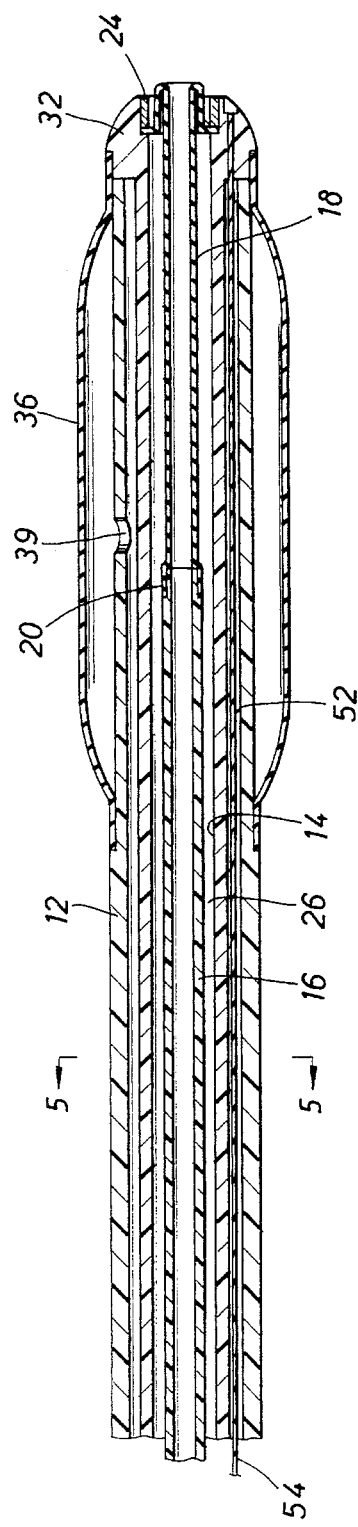
FIG. 6 is a sectional view of the forward end of the catheter system of the invention shown in FIG. 4 wherein the everting tube is shown in a fully retracted position.
Figure 7:
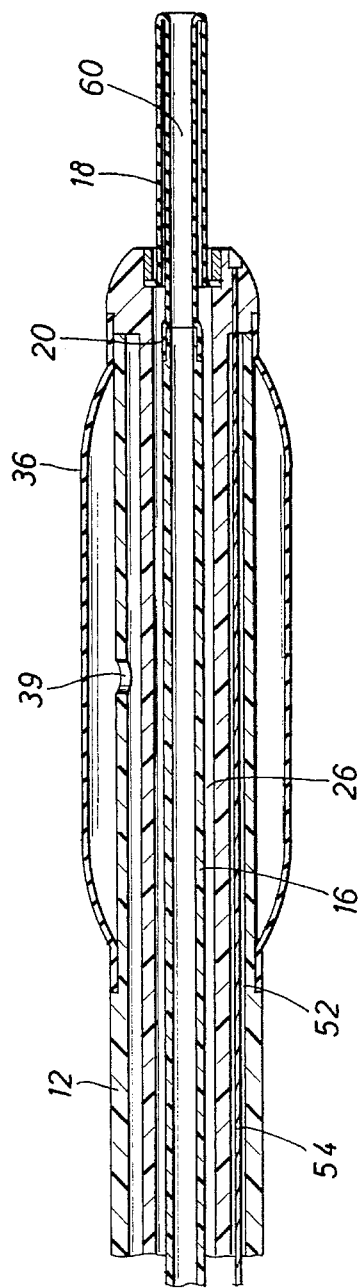
FIG. 7 is a sectional view of the forward end of the catheter system of the invention shown in FIG. 4 wherein the everting tube is shown in a fully extended position.
Figure 8:
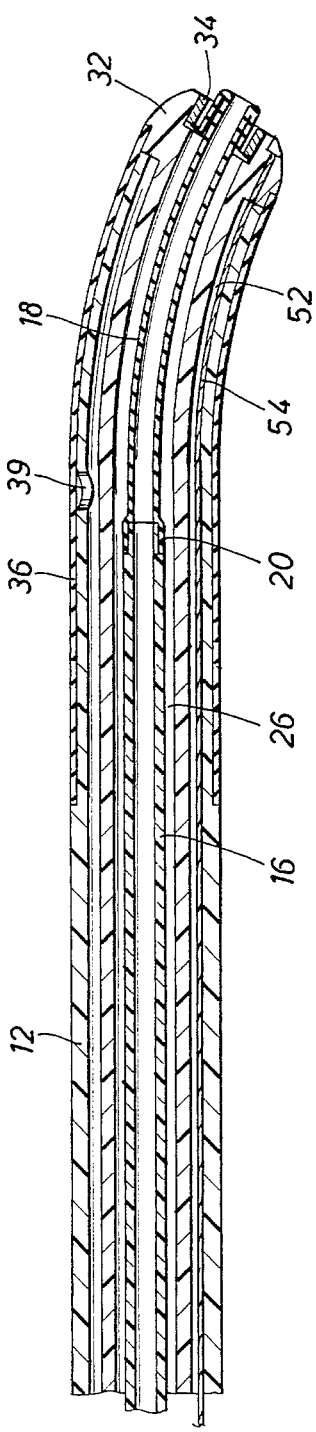
FIG. 8 is a sectional view of the forward end of the catheter system of the invention shown in FIG. 4 showing the actuator wire retracted for deflecting the forward end of the catheter shaft.

Referring now to FIGS. 4–8, an alternate embodiment of the catheter system of the invention is disclosed. For the sake of convenience, like reference numerals are employed to designate like components which have been previously identified. The embodiment of FIGS. 4–8 is substantially identical to the embodiment described in FIGS. 1–3. However, the catheter shaft 12, as best shown in FIGS. 6–7, includes a deflection wire lumen 52 extending along the catheter shaft 12 opposite the fluid lumen 34. A deflection wire 54 extends through the lumen 52. The distal end of the deflection wire 54 is embedded and bonded to the end 32 of the catheter shaft 12. The proximal end of the deflection wire 54 terminates at the Y-fitting 38 which is provided with an angularly extending connector 56. A thumb actuator connector 58 is threadably secured to the connector 56 and the terminal end of the deflection wire 54 extends through the connector 58 and a thumb or finger ring 59. Manipulation of the thumb actuator ring 59, for example by pulling back thereon, deflects the forward end of the catheter shaft 12, as shown in FIG. 8, so that it may be guided into a branch of the blood vessel or the like.

Referring now specifically to FIGS. 6 and 7, it will be observed that the slide catheter 16 and everting tube 18 are fully retracted within the catheter shaft 12. While in the retracted position as shown in FIG. 6, the catheter 12 is inserted into the patient's blood vessel or cavity. For example, the catheter 12 may be inserted into the femoral artery and advanced through the artery to the desired location. Sometimes, it is not possible to advance the catheter 12 to the site which requires treatment. For example, the blood vessel may be partially blocked, thereby limiting further advance of the catheter 12. The catheter 12 may also be too large to enter a branch blood vessel. If a partial blockage is encountered, it may be possible to expand the balloon 36 and thereby flatten plaque or the like against the blood vessel wall to open the blood vessel lumen sufficiently so that the catheter 12 may be advanced therethrough. In the event further advance of the catheter 12 is not possible the slide tube 16 is advanced within the catheter shaft 12 and fluid is injected in the annular space 26 causing eversion of the everting tube 18 from the leading end 32 of the catheter shaft 12. The slide tube 16 is advanced forwardly incrementally to provide slack in the everting tube 18 so that it everts outwardly under fluid pressure. The process is repeated until the everting tube 18 is fully everted as best shown in FIG.

7 or until the site of treatment of the blood vessel is reached. Once the site of treatment has been reached or the everting tube 18 has everted beyond the site of a partial obstruction, fluid pressure in the annulus 26 is discontinued or reduced, and medication may be introduced through the passage 60 defined by the slide tube 16 and everting tube 18. Alternatively, the passage 60 may be used to deliver other medical devices such as a catheter guide wire or a small fluid sampling tube to the treatment site.

After treatment has been terminated, the catheter shaft 12 may be withdrawn by releasing the pressure in the annulus 26 and the balloon 36, if any, and retracting the slide tube 16 so that the everting tube 18 is fully retracted within the catheter shaft 12. The catheter 12 may then be withdrawn from the blood vessel or artery in the normal way.

Referring now to FIGS. 9 and 10, another alternate embodiment of the catheter system of the invention is generally identified by the reference numeral 70. The catheter 70 is substantially identical to the catheters 10 and 50, previously described herein. Like reference numerals have been employed to identify like components. In the embodiment of FIGS. 9 and 10, a second dilatation balloon 72 is mounted at the distal end of the slide tube 16 in advance of the everting tube 18. The slide tube 16 is provided with a lumen 74 which is connected at the proximal end thereof (not shown in the drawings) to a fluid source for inflating the second dilatation balloon 72 as required. In the embodiment of FIGS. 9 and 10, the everting tube 18 is bonded to the slide tube 16 rearward of the second dilatation balloon 72 at point 20. When fully retracted as shown in FIG. 9, the slide tube 16, everting tube 18 and dilatation balloon 72 are carried within the catheter shaft 12. The dilatation balloon 72 may be utilized to expand the lumen of a small blood vessel so that relatively inexcessible regions of the vascular system may be reached for treatment.

Alternatively, and in the event the blood vessel is blocked by a blood clot, the forward tip 78 of the slide tube 16 may be utilized to penetrate the blood clot and irrigate the blood clot with fluid and medication in an effort to dissolve or dislodge the blood clot. Once the blood clot is loosened or separated from the blood vessel, the dilatation balloon 72 may be retained inflated while the entire catheter assembly is withdrawn from the blood vessel, thereby displacing and removing the blood clot from the vascular system.

While the invention herein is described in what is presently considered to be practical preferred embodiments thereof, it will be apparent that many modifications may be made within the scope of the invention, which scope is to be accorded the broadest interpretation of the appended claims so as to encompass all equivalent methods and apparatus.

While the foregoing is directed to the preferred and illustrated embodiments, the scope is determined by the claims which follow:

What is claimed is:

1. A toposcopic dilation catheter for insertion into a body passageway, comprising:

(a) a catheter shaft for inserting into the body passageway, wherein said catheter shaft includes a distal end, an outer surface and an axial passage extending therethrough;

(b) a slide tube coaxially positioned within said axial passage, wherein said slide tube includes a distal end;

(c) an everting tube carried within said axial passage, said everting tube having one end bonded to the distal end of said slide tube and the opposite end bonded to the distal end of said catheter shaft, wherein the everting tube may be everted under fluid pressure;

(d) first balloon means carried on the outer surface of said catheter shaft, wherein said balloon means may be expanded under fluid pressure;

(e) a deflection wire extending along the length of said catheter shaft, wherein said catheter shaft includes a passageway for receiving said deflection wire therethrough, said deflection wire having a leading end connected to the distal end of said catheter shaft and connected to a thumb actuator at the opposite end thereof for manipulating the distal end of said catheter shaft in an angular direction; and (f) second balloon means mounted at the distal end of said slide tube, wherein said one end of said everting tube is bonded to the distal end of said slide tube rearward of said second balloon means.

2. The apparatus of claim 1 including a fluid passageway extending the length of said catheter shaft, said fluid passageway having a proximal end adapted for connection to a fluid source and a distal end terminating at a port formed in the wall of said catheter shaft, and wherein said fluid passage is in fluid communication with the interior of said first balloon means through said port.

3. The apparatus of claim 1 wherein said everting tube may be incrementally advanced beyond the distal end of said catheter shaft upon applying fluid pressure on the everting tube through a lumen and upon forward advancement of said slide tube within said axial passage of said catheter shaft.

4. A toposcopic dilation catheter for insertion into a body passageway, comprising:

(a) a catheter shaft for inserting into the body passageway, wherein said catheter shaft includes a distal end, an outer surface and an axial passage extending therethrough;

(b) a slide tube coaxially positioned within said axial passage, wherein said slide tube includes a distal end;

(c) an everting tube carried within said axial passage, said everting tube having one end bonded to the distal end of said slide tube and the opposite end bonded to the distal end of said catheter shaft, wherein the everting tube may be everted under fluid pressure;

(d) first balloon means carried on the outer surface of said catheter shaft, wherein said balloon means may be expanded under fluid pressure; and (e) second balloon means mounted at the distal end of said slide tube.

5. In a catheter having an inner catheter shaft with a leading end and an outer surface, an everting flexible catheter tube bonded to said outer surface adjacent said leading end, and a balloon integral to said outer surface of said inner catheter shaft, a method of canalizing of blood clot in a blood vessel comprising the steps of:

(a) inserting the catheter into the blood vessel and advancing the leading end of the inner catheter shaft to the region of the blood clot;

(b) penetrating the blood clot with the leading end of the inner catheter shaft;

(c) inflating the balloon carried about the leading end of the inner catheter shaft; and (d) removing the blood clot by withdrawing the catheter from the blood vessel while the balloon is inflated.

6. The method of claim 5 including the step of irrigating the blood clot.

7. In a catheter device having an outer catheter shaft with a leading end and an outer surface, a slide tube with a leading end coaxially positioned within said outer catheter shaft, an everting flexible catheter tube having one end bonded to said leading end of the outer catheter shaft, a first balloon integral to said outer surface of said outer catheter shaft, a second balloon carried about the leading end of said slide tube, wherein the opposite end of said everting flexible tube is bonded to said slide tube rearward of said second balloon, a method of canalizing a blocked blood vessel comprising the steps of:

(a) inserting said outer catheter shaft into the blood vessel and advancing the leading end of the catheter shaft to the region of the blood clot;

(b) anchoring the outer catheter shaft in the blood vessel by expanding said first balloon under fluid pressure;

(c) everting said flexible outer catheter tube under fluid pressure and simultaneously advancing the leading end of said slide tube beyond the leading end of said outer catheter shaft;

(d) penetrating the blood vessel blockage with the leading end of said slide tube; and (e) inflating the second balloon to canalize the blood vessel.

8. The method of claim 7 further including the steps of irrigating the blood vessel and removing the blood vessel blockage by withdrawing the outer catheter shaft from the blood vessel while the second balloon is inflated.

* * * * *